(12) United States Patent
Chang (10) Patent No.: US 11,013,573 B2
(45) Date of Patent: May 25, 2021

(54) HEAD-MOUNTED ILLUMINATOR WITH CAPACITIVE PROXIMITY CONTROL

(71) Applicant: General Scientific Corp., Ann Arbor, MI (US)

(72) Inventor: Byung J. Chang, Ann Arbor, MI (US)

(73) Assignee: General Scientific/Surgitel, Ann Arbor, MI (US)

( * ) Notice: Subject to any disclaimer, the term of this patent is extended or adjusted under 35 U.S.C. 154(b) by 0 days.

(21) Appl. No.: 16/219,541

(22) Filed: Dec. 13, 2018

(65) Prior Publication Data

US 2019/0125482 A1 May 2, 2019

Related U.S. Application Data

(63) Continuation-in-part of application No. 16/017,778, filed on Jun. 25, 2018, which is a continuation-in-part
(Continued)

(51) Int. Cl.
*F21V 23/04* (2006.01)
*A61B 90/35* (2016.01)
(Continued)

(52) U.S. Cl.
CPC .............. *A61B 90/35* (2016.02); *A61B 90/30* (2016.02); *A61B 90/361* (2016.02); *F21L 4/00* (2013.01); *F21V 21/084* (2013.01); *F21V 23/003* (2013.01); *F21V 23/02* (2013.01); *F21V 23/0471* (2013.01); *G02C 11/04* (2013.01); *G06F 3/16* (2013.01); *G10L 15/22* (2013.01); *H04N 5/232* (2013.01);
(Continued)

(58) Field of Classification Search
CPC ..... H05B 37/0236; G06F 3/167; A61B 90/30; A61B 2090/502; A61B 2017/00203; G10L 15/22; G10L 2015/223; F21V 21/084; F21V 33/0052; H04N 5/23296
See application file for complete search history.

(56) References Cited

U.S. PATENT DOCUMENTS

2008/0310145 A1* 12/2008 Blake ..................... A61B 90/35
362/105
2012/0275140 A1* 11/2012 Feinbloom ............. H05B 47/19
362/105
(Continued)

*Primary Examiner* — Evan P Dzierzynski
(74) *Attorney, Agent, or Firm* — Law Offices of John G. Posa (57) ABSTRACT

Head-mounted accessories for surgeons and medical/dental practitioners are equipped with no-touch controls including, in different embodiments, passive and active infrared detection, voice operation, and capacitive proximity control. Compared to infrared, capacitive proximity control may be more omni-directional, whereas IR, particularly active IR, tends to be more effective in a cone of operation. Compared to voice activation, capacitive sensing is less expensive and less prone to false activation based upon ambient noise or other voices. The invention may be used to control other medical/dental accessories such as a head-mounted video camera, in which case the controller is further operative to at least turn the video camera ON or OFF. More preferably, a controller is additionally operative to control the focus or zoom of the video camera in accordance with touch-free commands.

18 Claims, 9 Drawing Sheets

Related U.S. Application Data of application No. 15/136,380, filed on Apr. 22, 2016, now Pat. No. 10,066,816, which is a continuation-in-part of application No. 14/302,899, filed on Jun. 12, 2014, now abandoned, which is a continuation-in-part of application No. 13/929,394, filed on Jun. 27, 2013, now abandoned.

(51) Int. Cl.
| | |
|---|---|
| *F21V 21/084* | (2006.01) |
| *F21V 23/00* | (2015.01) |
| *F21V 23/02* | (2006.01) |
| *G10L 15/22* | (2006.01) |
| *A61B 90/00* | (2016.01) |
| *F21L 4/00* | (2006.01) |
| *G02C 11/04* | (2006.01) |
| *A61B 90/30* | (2016.01) |
| *G06F 3/16* | (2006.01) |
| *H04N 5/232* | (2006.01) |
| *H05B 47/12* | (2020.01) |
| *H05B 47/105* | (2020.01) |
| *F21W 131/202* | (2006.01) |
| *F21Y 115/10* | (2016.01) |
| *A61B 17/00* | (2006.01) |
| *A61B 90/50* | (2016.01) |

(52) U.S. Cl.
CPC ........... H05B 47/105 (2020.01); H05B 47/12 (2020.01); *A61B 2017/00203* (2013.01); *A61B 2017/00734* (2013.01); *A61B 2090/309* (2016.02); *A61B 2090/3616* (2016.02); *A61B 2090/502* (2016.02); *F21W 2131/202* (2013.01); *F21Y 2115/10* (2016.08); *G10L 2015/223* (2013.01)

(56) References Cited

U.S. PATENT DOCUMENTS

2014/0191664 A1\* 7/2014 Johnson ............... A61C 1/0015
315/152
2019/0113216 A1\* 4/2019 Smith ................. F21V 23/0471

\* cited by examiner

HEAD-MOUNTED ILLUMINATOR WITH CAPACITIVE PROXIMITY CONTROL

REFERENCE TO RELATED APPLICATIONS

This application is a continuation-in-part of U.S. patent application Ser. No. 16/017,778, filed Jun. 25, 2018, which is a continuation-in-part of U.S. patent application Ser. No. 15/136,380, filed Apr. 22, 2016, which is a continuation-in-part of U.S. patent application Ser. No. 14/302,899, filed Jun. 12, 2014, which is a continuation-in-part of U.S. patent application Ser. No. 13/929,394, filed Jun. 27, 2013, the entire content of all of these applications being incorporated herein by reference.

FIELD OF THE INVENTION

This invention relates generally to headlights and other accessories used by surgeons, medical and dental practitioners and, in particular, to touch-free controls for such headlights and other accessories.

BACKGROUND OF THE INVENTION

It is common for surgeons and medical/dental practitioners to wear headlights to enhance vision. Typical headlights using light-emitting diodes and optical fibers may be found at http://surgitel.com/headlights.

With such systems, the headlight contains only the light source and beam-forming optics. The power supply is disposed remotely, and may be belt-worn, for example.

One of the problems with existing systems is that the control unit may not be sterilized, such that the practitioner's hand may become contaminated if the light is turned ON or OFF during a procedure.

SUMMARY OF THE INVENTION

This invention resides in head-mounted accessories for surgeons and medical/dental practitioners with no-touch controls including, in different embodiments, passive and active infrared detection, voice operation, and capacitive proximity control. Compared to infrared, capacitive proximity control may be more omni-directional, whereas IR, particularly active IR, tends to be more effective in a cone of operation. Compared to voice activation, capacitive sensing is less expensive and less prone to false activation based upon ambient noise or other voices. The invention may be used to control other medical/dental accessories such as a head-mounted video camera, in which case the controller is further operative to at least turn the video camera ON or OFF. More preferably, a controller is additionally operative to control the focus or zoom of the video camera in accordance with touch-free commands.

A head-mounted illuminator system with no-touch controls according to the invention includes a battery unit including one or more batteries providing DC power, and head-mounted components, physically remote from the battery unit. The head-mounted components may include a capacitive proximity sensor with a metal sensing surface, a power switch and an LED illuminator. DC power is provided to the power switch through the battery unit, and the capacitive proximity sensor is operative to control the power switch to toggle the LED illuminator between an ON condition and an OFF condition when a human hand is placed proximate to the metal sensing surface.

In a preferred embodiment, at least the LED illuminator is disposed in a housing that includes the metal sensing surface of the capacitive proximity sensor. More preferably, the capacitive proximity sensor, power switch, and LED illuminator are disposed in a common housing that includes the metal sensing surface. Further, only DC power and ground wires are used to interconnect the battery unit to the head-mounted components.

The battery unit may include a brightness control that varies the level of DC power provided to the power switch. A separate coupler unit operative may be used to interconnect the capacitive proximity sensor, power switch and LED illuminator. The system may further include apparatus for mounting the LED illuminator to a pair of eyeglass frames or to a headband. The head-mounted components may additionally include a proximity distance adjustment control to adjust activation distance in the range of 1-5 cm, more preferably in the range of 2-3 cm.

DETAILED DESCRIPTION OF THE INVENTION

This invention is directed to headlights and other accessories that utilize technology enabling ON and OFF operation and other controls without physical contact. As such, the invention is ideally suited for surgical, medical and dental applications to protect a sterile field that could be compromised through manual contact. As disclosed herein, this no-contact operation may be based upon passive or active infrared, voice recognition, or capacitive proximity control.

Figures 1, 2:
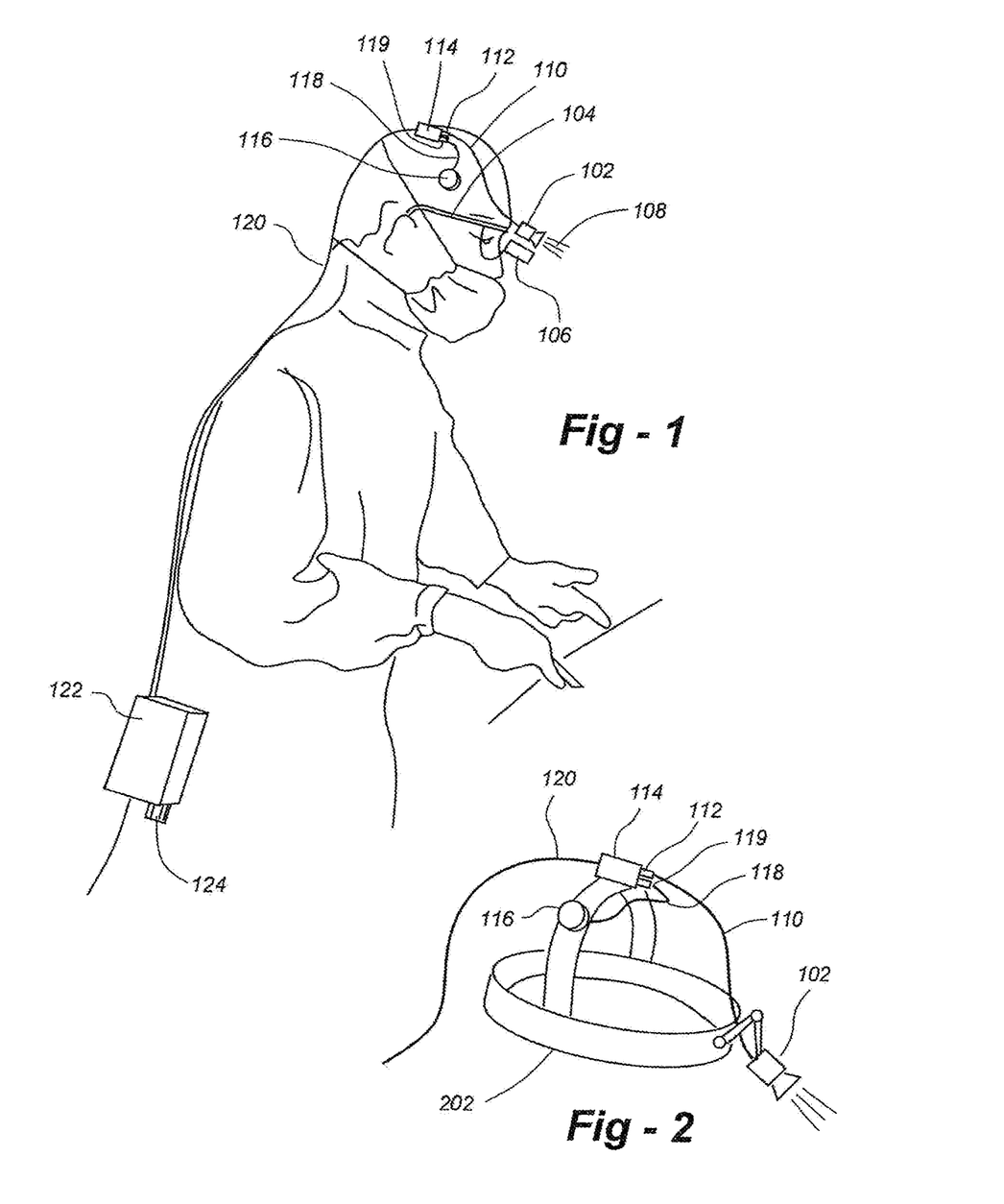
FIG. 1 is a drawing of an embodiment of the invention using an eyeglass frame mounted headlight.
FIG. 2 is a drawing of an embodiment of the invention using headband-mounted headlight.

In preferred embodiments, the light source comprises one or more light-emitting diodes (LEDs). FIG. 1 is a drawing of an embodiment of the invention using an LED headlight 102 mounted to eyeglass frames 104. In all embodiments, the light source may be permanently connected or temporarily coupled by way of a clip-on structure. Loupes 106, either the flip-up type or through-the-lens (TTL) type may be provided in conjunction with light source 102.

The light source 102 includes beam-forming and/or focusing optics (not shown) to produce a desired beam pattern 108. The LED(s) are controlled through cable 110 which is connected to remote power supply and controller 122, which may be belt-worn, through cable 120. The system also includes an infrared (IR) sensor module 116. While the light 102 and IR sensor 116 may be connected to the unit 122 directly, in the preferred embodiment, cable 110 from the light connects to a coupling unit 114 through electrical connector 112, and cable 118 from the sensor connects to the coupling unit 114 through electrical connector 119, enabling either or both of the cables 110, 118 to be disconnected. The power supply and control unit 122 contains rechargeable batteries that are replenished via connect to a changer shown in the block diagram of FIG. 3. A manual control knob 124 may be provided to establish a desired level of brightness prior to ON/OFF control using the IR sensor.

The IR sensor in this embodiment may comprise a miniature passive IR sensor available from various suppliers. For example, the KC7783 PIR Sensor Module is a pyroelectric sensor module developed for human body part detection. A PIR detector, combined with a Fresnel lens, are mounted on a compact printed circuit board together with an analog IC (the KC778B) providing a TTL output that can be directly connected to a microcontroller or logic device disposed in remote unit 122. Again, this PIR sensor is one of many applicable to the invention.

The IR sensor may be mounted at any convenient location, though in the preferred embodiment, it is head-mounted, whether clipped to a head mask or other clothing, mounted on eyeglass frames, the light source itself, or a headband 202 of the type depicted in FIG. 2. The sensor is preferably oriented in a direction that is least likely to experience false activation from bright/warm lights, other individuals, and so forth.

In operation, a user places their hand in the proximity of the sensor 116, which causes the light 102 to turn ON and OFF without physical contact. In the preferred embodiment, the detection distance of the sensor is adjusted to be on the order of about 5 to 10 cm to enhance proper operation. This activation distance, as well as the field of view, may be adjusted through electrical component selection and/or sensor lens optics, materials, translucency, and so forth.

Figure 3:
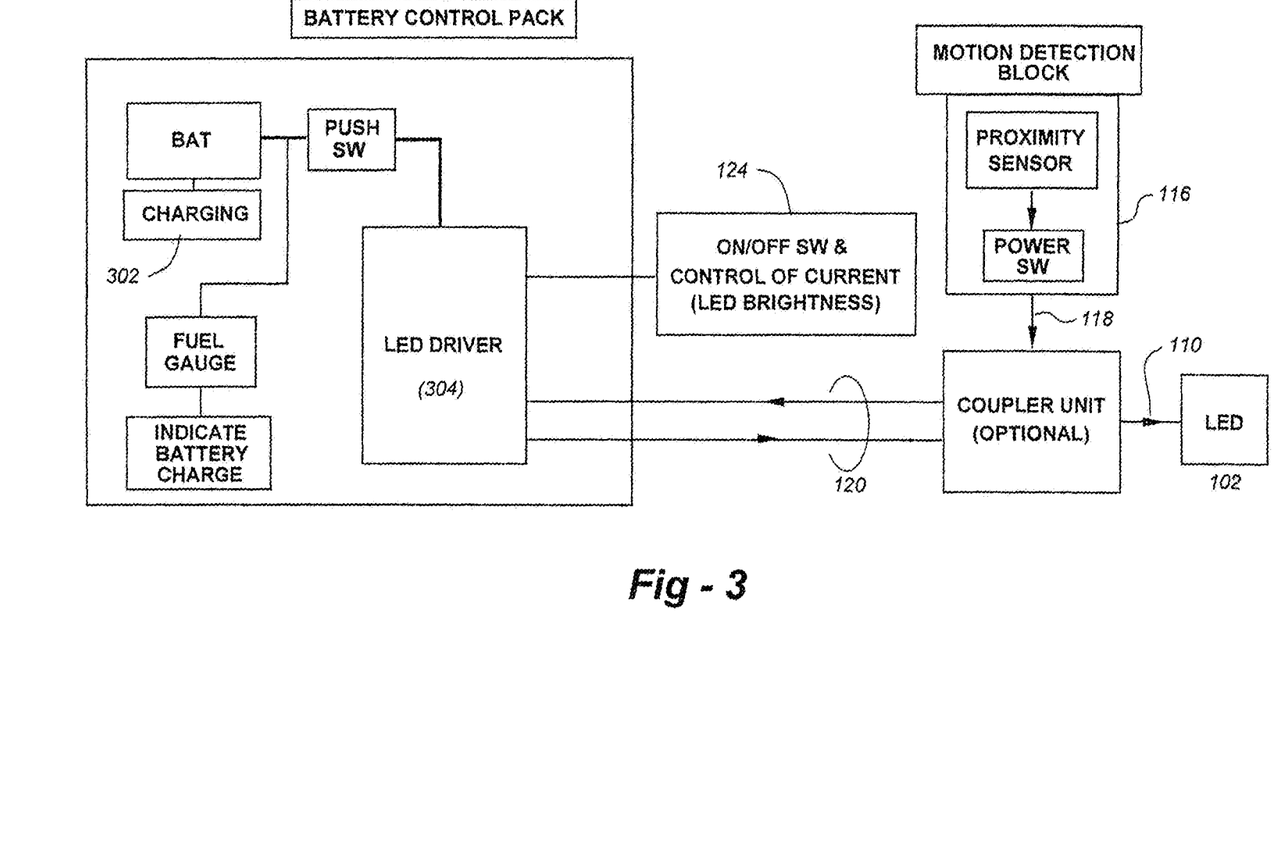
FIG. 3 is a block diagram of the invention showing cables, light emitter, and sensor.

Referring to FIG. 3, electrical circuitry 304 in the power supply and control unit 122 may be designed to simply toggle the light ON/OFF with each hand/body part detection. In other words, if the light is ON, the user brings their hand near the sensor to turn it OFF, and vice-versa. Further, if the light is ON or OFF by mistake, one movement of the hand may be used to reset the light to the desired state.

Figure 4:
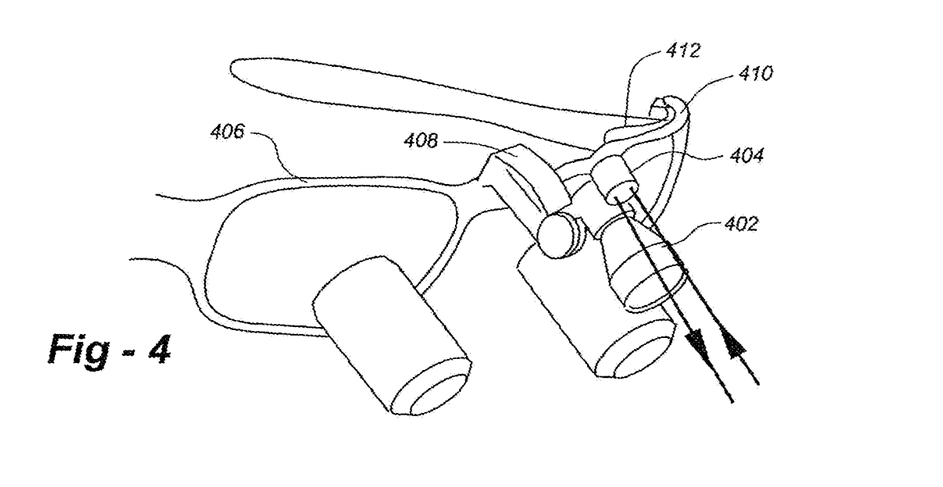
FIG. 4 is a drawing that illustrates an embodiment of the invention using an active IR sensor with a variable threshold to customize the activation distance.

FIG. 4 is a drawing that illustrates an embodiment of the invention using an active infrared sensor as opposed to a passive unit. The difference here is that the sensor, mounted in housing 404, includes a light emitter and detector as opposed to merely an IR detector. The housing 402 includes\ an LED light source which is coupled to eyeglass frames 406 through mechanically adjustable coupler 408. The frames 406 are shown with through-the-lens loupes though the invention is not limited by the choice of loupes, coupler or particular light unit. The optical orientation of the optical proximity sensor is preferably aligned with the optical axis of light 402 though this is also not necessary as a user may desire sidewise control. Cables 410, 412 may be routed to separate power sources to power the LED light source and/or control unit for the proximity detector 404.

Figure 5:
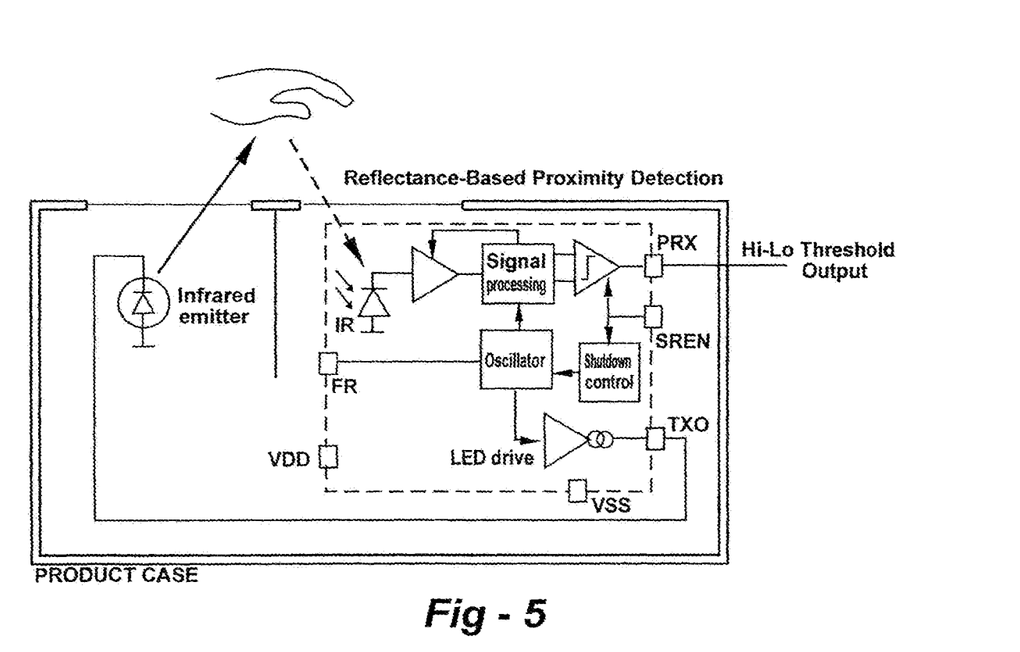
FIG. 5 is a block diagram of an optical proximity detector applicable to the invention.
Figure 6:
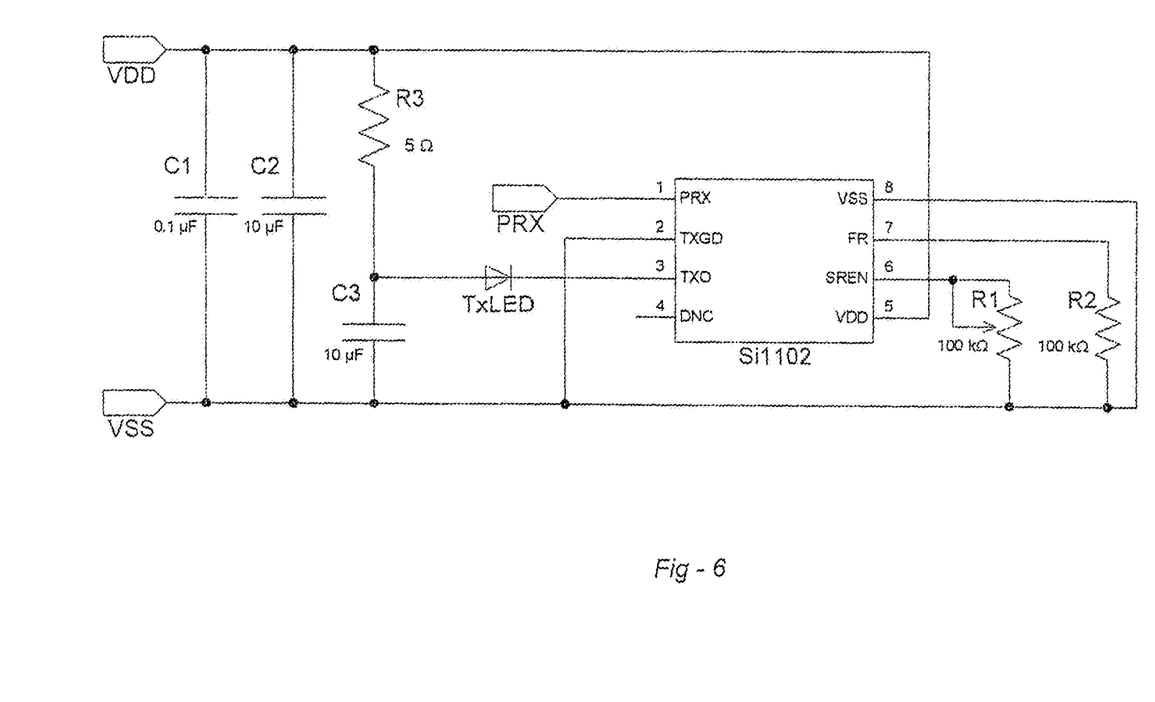
FIG. 6 is a schematic depicting how the detector of FIG. 5 may be implemented.

FIG. 5 is a block diagram of the optical proximity detector, which in this case happens to be a Si1102 device made by Silicon Labs. Comparable units from other manufacturers may be substituted. FIG. 6 is a schematic depicting how the detector of FIG. 5 may be implemented. The Si1102 is an active optical reflectance proximity detector with a simple on/off digital output whose state is based upon the comparison of reflected light against a set threshold. An LED sends light pulses whose reflections reach a photodiode and are processed by the Si1102's analog circuitry. If the reflected light is above the detection threshold, the Si1102 asserts the active-low PRX output to indicate proximity. The potentiometer, R1, is used to set the proximity detection threshold.

The Si1102 circuit periodically detects proximity at a rate that can be programmed by a single resistor (R2). Although the thresholds are normally set using a potentiometer for R1 (or R2), it is possible to digitally control various resistance values by using MCU GPIO pins to switch-in different value resistors (or parallel combinations of resistors). Regardless of which resistor(s) are used to control activation proximity, they may be located on unit 404 or remotely in the power supply/control unit for the sensor unit. In the preferred embodiment, a user is able to adjust the ON/OFF proximity of a hand, for example, to be in the range of one to 12 inches or more.

Figure 7:
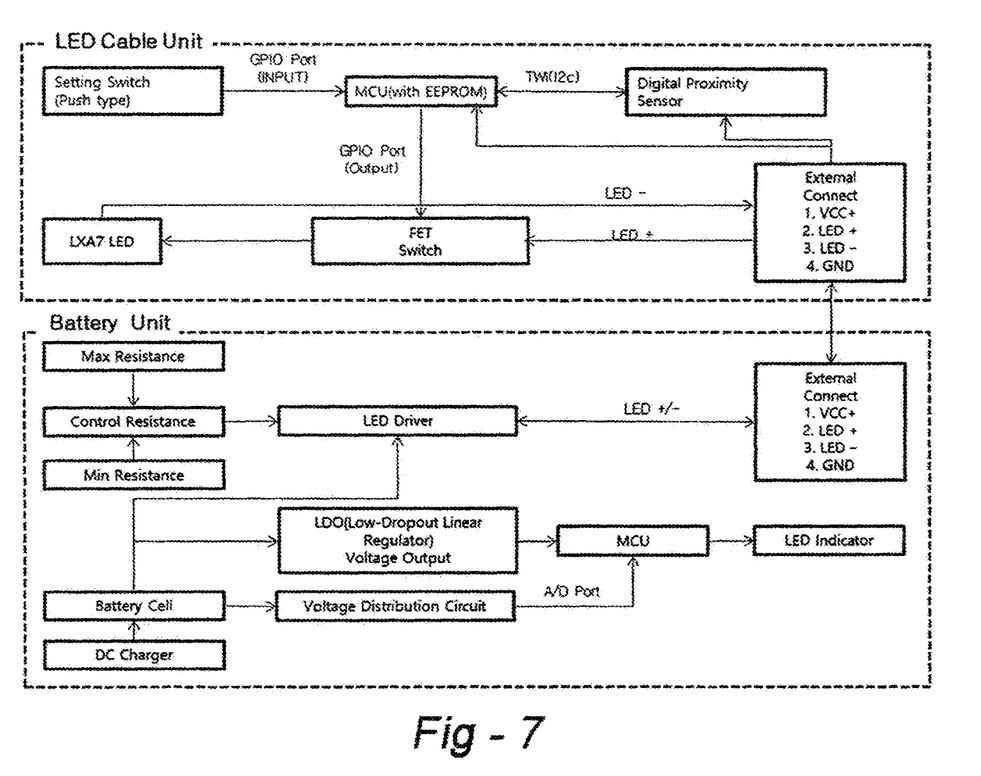
FIG. 7 is a block diagram of a microprocessor-based (MCU) version of a motion-activated LED headlamp controller with proximity adjustment.

FIG. 7 is a block diagram of a microprocessor-based (MCU) implementation of a motion-activated LED headlamp controller which may include proximity distance adjustment. Note that in this and in other embodiments, all of the electronics associated with proximity control of the LED is disposed in LED Cable Unit, such that only power signals are delivered to the LED Cable Unit through cables from the Battery Unit. In particular, an External Connect in the Battery Unit delivers LED +/− power as well as VCC+ and ground to power the MCU and other components in the LED Cable Unit.

As with other embodiments disclosed herein, by placing all proximity ON/OFF and threshold controls at the location of the LED light source, no feedback or control signals need to be routed from the LED Cable Unit back to the Battery Unit. Thus, in the configuration of FIG. 4, only a power cable needs to be routed from the Battery Unit to the sensor 404 and LED source 402. Particularly when the LED brightness control is located on the remote battery unit, it may be advantageous to run multiple power lines (plus ground) from the battery unit to the head-mounted unit, as this allows dimming with a separate power line being used to control lower-current circuitry in the head-mounted unit. However, if brightness control is not provided or desired, only two wires are needed from the power supply to the head-mounted unit, one for power and one for ground. In this configuration, power to control electronic circuitry made be derived from the same line used to power the LEDs, with a suitable power supply. As a further alternative, brightness control may be provided in the head-mounted unit, again requiring only power and ground from the battery pack, whether remote or coupled to the head-mounted unit.

Figure 9:
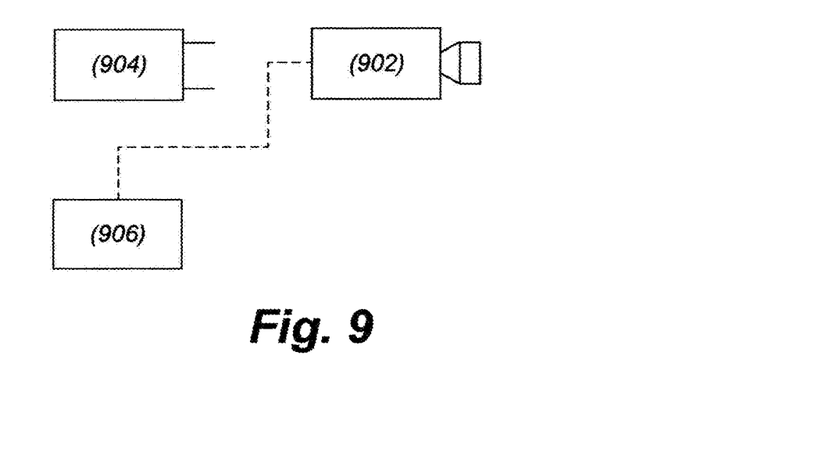
FIG. 9 shows how a head-mounted unit may be interconnected to a remote battery unit and/or a directly coupled rechargeable battery unit, resulting in a wireless, entirely self-contained head-mounted unit.

As shown in FIGS. 3 and 7, an advantage of embodiments of the invention is that only power and ground wires are required between a remote battery unit and the head-mounted unit, thereby eliminating the need for control signals to be routed to the battery unit. Another advantage is that the power supply need not be remote, and may be physically coupled directly to the head-mounted unit. As shown in FIG. 9, the same head-mounted unit 902 may accept a physically coupled rechargeable battery pack 904, or may be connected to a remote source 906, as previously described. The attachment of battery 904 converts the system into a completely wireless head-mounted light.

As mentioned, all embodiments of the invention may be optionally equipped with variable proximity in terms of sensitivity/distance. In the block diagram of FIG. 7, an EEPROM associated with the MCU stores the threshold value enabling the Proximity Sensor (PS) to turn the FET Switch (and LED light) ON and OFF. If the signal from the PS becomes stronger than the stored threshold value, the MCU is operative to turn the FET and LED ON and OFF. If a user desires a different activation distance, they can replace the existing threshold value using the pushbutton Setting Switch. When this reset button is pushed, the MCU detects the signal reflected from an object (such as hand) at a desired activation distance and stores this new criteria value in the EEPROM of the MCU. The resetting function will allow users to decide their desirable activation distance.

Figure 8:
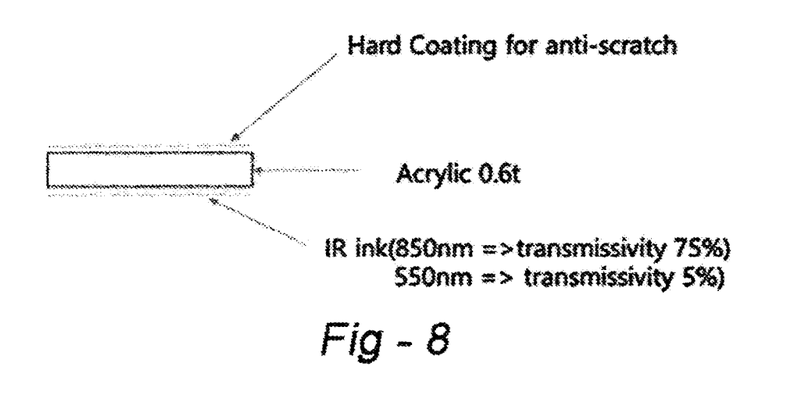
FIG. 8 is a cross section of an absorption-type IR filter applicable to the invention.

The LED light source includes an internal IR LED (about 900 nm), with IR filters being used to block stray IR signals from outside light sources such as room lights and dental or surgical overhead lights. Applicable IR filters have a high transmissivity for the internal IR wavelength and the low transmissivity for other wavelengths. Without the use of such filters the signal detection distance may vary significantly. FIG. 8 is a cross section of an absorption-type IR filter applicable to the invention, with the understanding that other types of filters may be used so long as they have a high transmissivity for the internal IR wavelength and the low transmissivity for other wavelengths.

Figure 10:
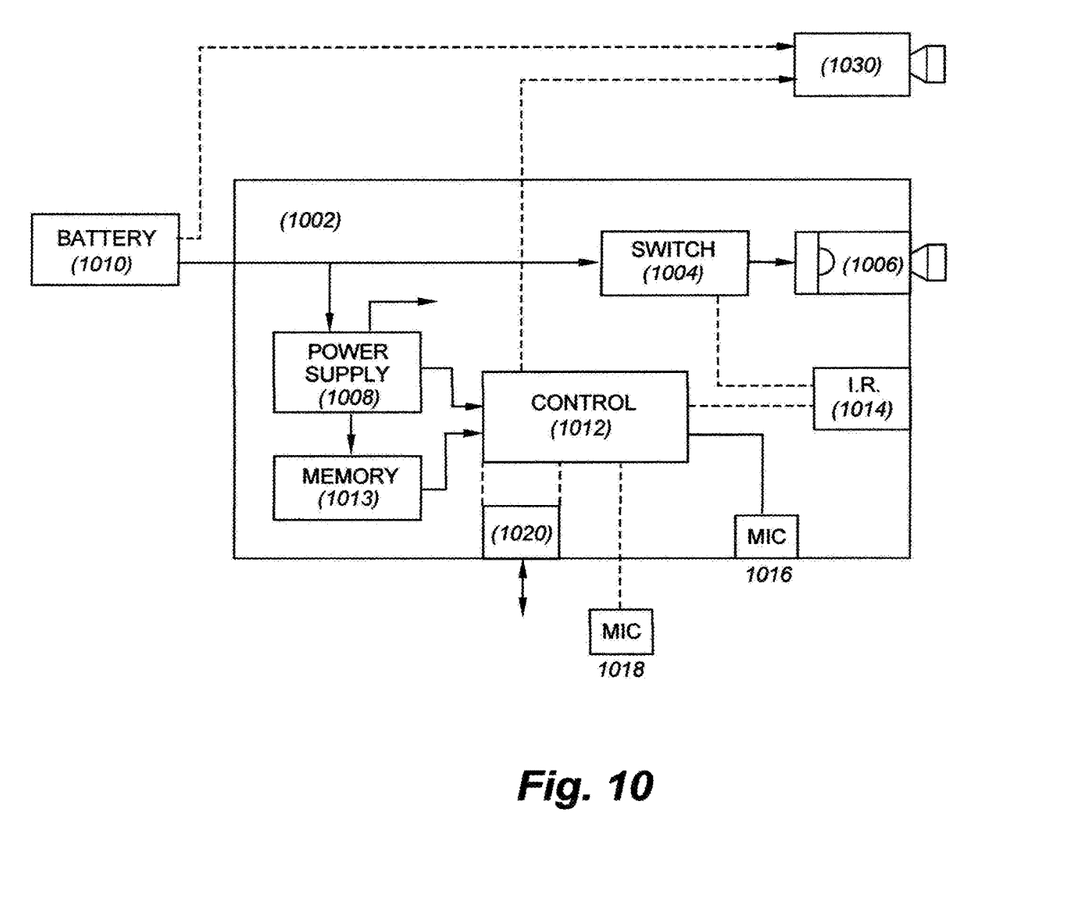
FIG. 10 is a block diagram showing important components associated with a voice-activated embodiment of the invention.

In alternative embodiments of the invention, voice control may be used instead of, or in conjunction with, infrared sensing. FIG. 10 illustrates an embodiment of the invention that includes speech recognition and voice command control. The head-mounted unit, 1002, preferably includes a power switch 1104 used to route power from rechargeable battery supply 1010 to light emitter(s) 1006. Again battery unit 101 may be remote or physically coupled to the head-mounted unit 1002. If separate power lines are not provided from the battery unit 1010, a power supply 1008 may be used to power electronic circuits in the head-mounted unit 1002, such as a microcontroller 1012. The microcontroller 1012 may be of conventional available design, and may have an internal memory or separate memory 1013 for storing command-related programs.

A passive or active infrared sensor 1014 may be provided to control switch 1004, though voice recognition is preferably used instead. Those of skill will appreciate that voice control may be provided in the form of a separate integrated circuit or module, as available from numerous sources such as Sensory, Inc. of Santa Clara, Calif., or software may be provided for execution by controller 1012. Again, such software is also available from various sources. A wired or wireless interface 1020 to a computer may be provided for programming purposes. The voice recognition may be speaker-independent or speaker-dependent, in which case the interface and computer may be used for voice-training purposes.

One or more microphones may be provided to capture speech from the user for control purposes, including microphone 1016 mounted on the head unit 1002, and/or one or more remote mics 1018, which may mounted on eyeglass frames, a headband, or support arm to bring the mic closer to the mouth of a user.

In a most basic configuration, the user would be able to turn the headlamp on and off with respective spoken commands "ON" and "OFF." To avoid false commands and provide for other functions as described below, a preamble may be used, such as "LIGHT—ON" and "LIGHT—OFF." If brightness control is provided, commands such as "LIGHT—BRIGHTER" and "LIGHT—DIMMER" may be used.

In addition to voice-activated headlamp control, the invention may be used to control other accessories such as video camera 1030, in which case commands such as "CAMERA—ON," "CAMERA—OFF," "CAMERA—ZOOM IN(/OUT)," "CAMERA—FOCUS," and so forth. Although FIG. 10 shows the camera connected to the head-mounted unit 1002 to use controller 1012, the voice-activated camera controls may be provided in unit 1030 with or without a headlamp.

As mentioned, the voice-activated control may be used with or without an I.R. sensor 1014. One use for both is in setting threshold control. For example, a user may place her hand at a particular distance from sensor 1014, and speak the command(s) "LIGHT—ON" or "LIGHT OFF" to set the distance the user wants to turn the light on and/or off using their hand. A user may place their hand at a desired distance from the sensor 1014 and speak "CAMERA FOCUS" to set a particular focus point for a video camera.

Figure 11:
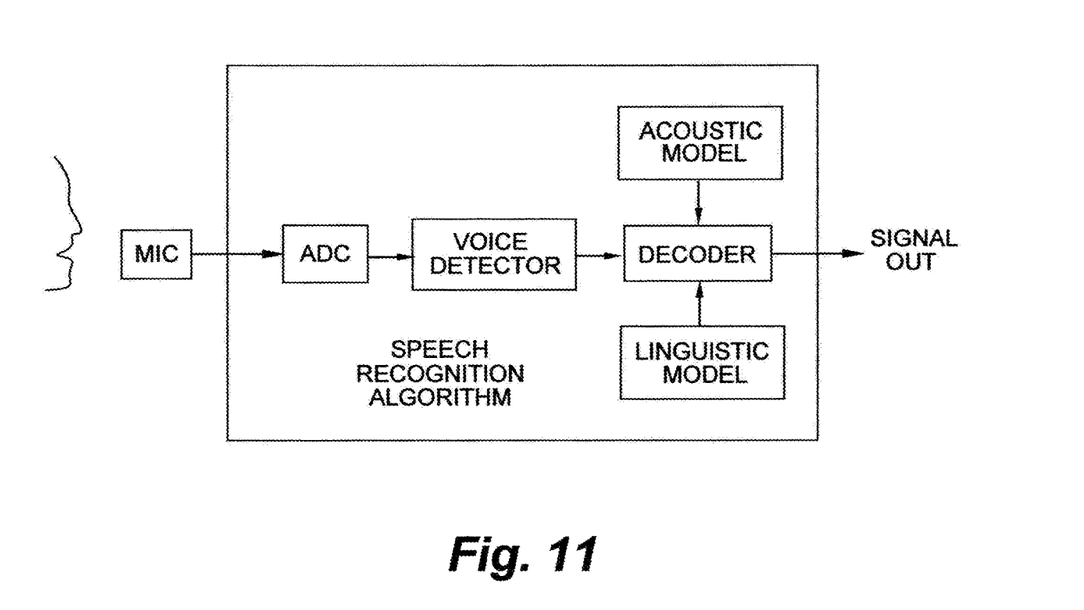
FIG. 11 is a block diagram of voice-activated components and algorithms applicable to the invention.

FIG. 11 is a block diagram specific to voice-activated components applicable to the invention. Specifically, the voice of a user is detected by a microphone, and an electrical signal representative of the user's speech is converter from analog to digital form by the A-D converter. The digitized signal is delivered to a voice detector which may receive inputs from both an acoustic model and a linguistic model. After the speech is recognized, a signal is output through a decoder, enabling the speech to function as a command in accordance with this invention.

As further alternative, capacitive proximity control may be used in conjunction with, or instead of, infrared or voice control. Capacitive proximity control has certain advantages over the alternatives. Compared to infrared, capacitive proximity control may be more omni-directional, as described in further detail below, whereas IR, particularly active IR, tends to be more effective in a cone of operation. Compared to voice activation, capacitive sensing is less expensive and less prone to false activation based upon ambient noise or other voices.

Figure 12:
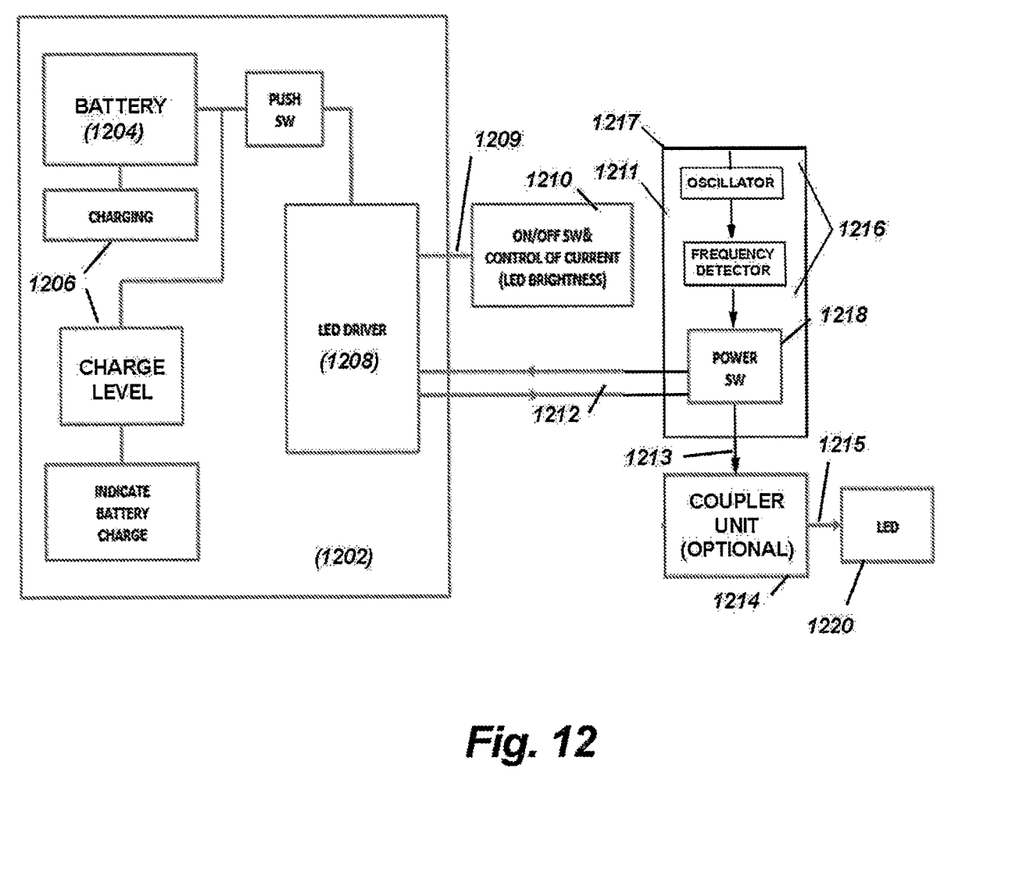
FIG. 12 is a block diagram illustrating an embodiment of the invention that utilizes capacitive proximity control.

FIG. 12 is a block diagram of a head-mounted LED illuminator that operates through capacitive proximity control. The system includes a battery unit 1202 that provides power to LED(s) 1220. The battery unit 1202 is worn on a user, typically through a belt connection. In addition to rechargeable batteries 1204, battery unit 1202 may contain various charge level circuits and/or battery level indicator. The batteries 1204 provide power to LED(s) 1220 through cables 1212 and through optional coupler unit 1214.

Continuing the reference to FIG. 12, battery unit 1202 further includes various user controls, such as ON/OFF switches, and LED brightness control 1210. While block 1210 is shown as a separate box interconnected to unit 1202 through wires 1209, in practice these controls may be integrated into or mounted on battery unit 1202.

LEDs 1220 may be head-mounted through any known fixture including without limitation clip-on or fastened to eyeglass frames or a headband as respectively shown in FIGS. 4 and 2. A sensor module 1211 includes a capacitive proximity sensor 1216 that drives a power switch 1218, preferably a solid-state field-effect transistor (FET). Power switch 1218, in turn, couples power from battery unit 1202 to LED(s), whereby the LED(s) are turned ON and OFF in response to the state of capacitive proximity sensor 1216 and power switch 1218.

A coupler unit 1214 may be provided to enhance connection versatility, allowing a physically separate sensor module 1211 and remote headlamp with LED(s) to plug into the coupler unit through cables 1213, 1215. Alternatively, and more preferably, LED(s) 1220 may be integrated with sensor module 1211 without a coupler unit, resulting in a single head-mounted unit with LED(s) 1220. As such, the configuration only includes two physically separate modules, belt-worn battery unit 1202, and a head-worn unit containing the capacitive proximity sensor 1216 and LED(s) 1220, similar to the arrangement shown in FIG. 4.

Further, as with other embodiments disclosed herein, by locating the sensor in close proximity to the LED illuminator, only power and ground wires need to be used between the battery unit 1202 and a head-worn unit. While separate power and ground wires may be used for the LED and the control electronics and sensor in the head-worn-unit, in the preferred embodiment, only one DC power and ground connection is made between the battery unit 1202 and the head-worn unit to simplify wiring and interconnections, thereby reducing cost and enhancing reliability.

The capacitive proximity sensor may be configured as a conventional circuit, including a metal sensing surface 1217 coupled to an oscillator and a frequency detector. The metal sensing surface acts as an antenna. The presence of a nearby object, such as a human hand, is sensed by the metal sensing surface, altering the oscillator frequency, and this change is detected by the frequency detector. The output of the frequency detector, in turn, drives the control electronics and, ultimately, the LED(s). While a separate metal sensing surface may be provided in accordance with the invention, advantageously, in the preferred embodiment, some or all of the housing of the head-worn unit is used as the sensing surface, thereby facilitating omni-directional control with a casing that is preferably already metal in construction.

In the preferred embodiment, the capacitive sensor module is implemented with an IQS127D integrated circuit available from Azoteq, Inc. The module integrates a fully integrated capacitive sensor having dual outputs—Physical Contact (Touch) and Proximity output. In accordance with this invention, both physical proximity and touch may be used to control the same functions, such as ON/OFF or, alternatively, touch may be used for a different function such as proximity distance control. For example, with one hand touching the control surface the other hand may be positioned at a desired control distance, whereby removed the touching hand stores this distance in a look-up memory in communication with the capacitive sensor module. Alternatively, the amount of time that a user keeps touching the control surface may be used for distance or mode control; i.e., touching for a predetermined number of seconds may change distance or mode settings. As a further alternative, a manual push-button may be used for distance or mode control, in which case a single-channel IQS127 chip may be used.

In any case, the LED itself may be used to provide feedback regarding mode or distance settings. For example, the LED may come ON to indicate ON distance setting, OFF to indicate OFF distance setting, or the LED may flash one or more times to indicate a change in mode or distance settings.

Figure 13:
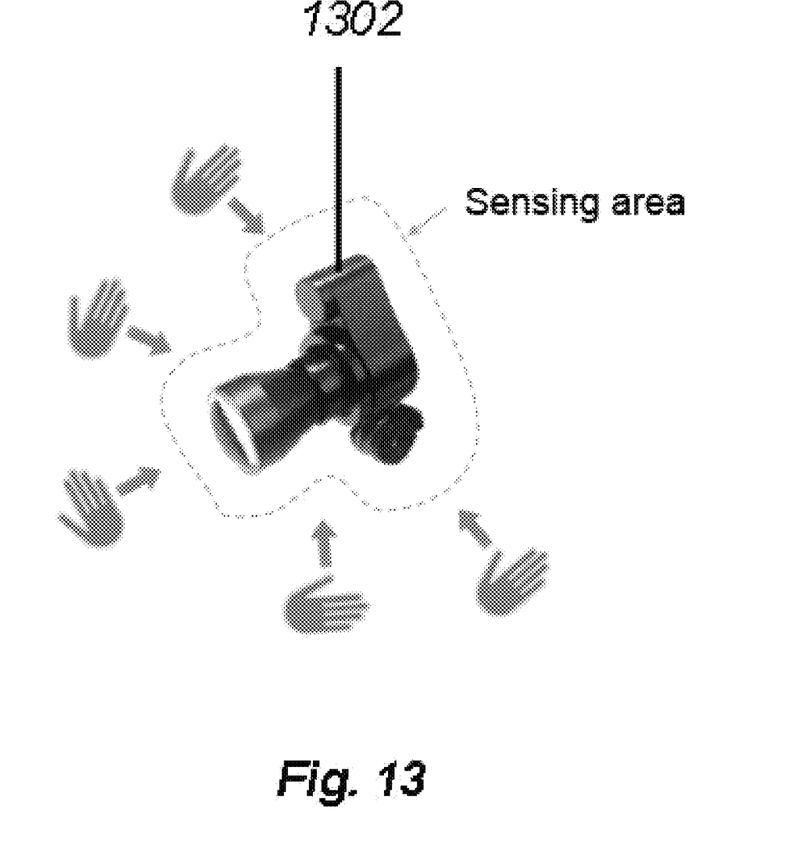
FIG. 13 is a drawing that depicts a head-mounted lamp structure applicable to the invention.

As shown in FIG. 13, using a capacitive proximity sensor detects all-around or nearly all-around the head-mounted LED body 1302. The maximum operating distance is in the range of 1 to 5 cm, more preferably 2 to 3 cm, and may be adjusted as described above. Other metallic surfaces may be used with or in place of the LED housing for capacitive control. For example, portions of a headband may incorporate one or more metal control surfaces; portions of eyeglass frames may incorporate one or more metal control surfaces; portions of the coupler unit; and so forth.

In addition to all-around sensing and low cost, the invention may be provided with a 'flicker-proof' function that prevents unwanted oscillation or "chattering." An auto-calibration function may also be provided for noise isolation. Further, the invention may be used with other head-mounted units, including video cameras, wherein the case of the camera may be used as part of the capacitive proximity sensor.

The invention claimed is:

1. A head-mounted illuminator system with capacitive control, comprising:
    a battery unit including one or more batteries providing DC power;
    head-mounted components, physically remote from the battery unit, and wherein the head-mounted components including the following:
        a capacitive proximity sensor coupled to a metal sensing surface;
        a power switch separate from the capacitive proximity sensor; and
        an LED illuminator; and
    wherein the DC power is provided to the power switch, and the capacitive proximity sensor is operative to control the power switch to toggle the LED illuminator between an ON condition and an OFF condition when a human hand is positioned proximate to the metal sensing surface.

2. The head-mounted illuminator system of claim 1, wherein at least the LED illuminator is disposed in a housing that includes the metal sensing surface.

3. The head-mounted illuminator system of claim 1, wherein only DC power and ground wires are used to interconnect the battery unit to the head-mounted components.

4. The head-mounted illuminator system of claim 1, wherein the capacitive proximity sensor, power switch, and LED illuminator are disposed in a common housing that includes the metal sensing surface.

5. The head-mounted illuminator system of claim 1, wherein the battery unit includes a brightness control that varies the level of DC power provided to the power switch.

6. The head-mounted illuminator system of claim 1, further including a coupler unit operative to interconnect the capacitive proximity sensor, power switch and LED illuminator.

7. The head-mounted illuminator system of claim 1, further including apparatus for mounting the LED illuminator to a pair of eyeglass frames.

8. The head-mounted illuminator system of claim 1, further including apparatus for mounting the LED illuminator to a headband.

9. The head-mounted illuminator system of claim 1, wherein the head-mounted components include a proximity distance adjustment control.

10. The head-mounted illuminator system of claim 9, wherein the proximity distance control is in the range of 1-5 cm.

11. The head-mounted illuminator system of claim 9, wherein the proximity distance control is in the range of 2-3 cm.

12. The head-mounted illuminator system of claim 1, wherein capacitive proximity sensor is operative to differentiate between non-contact sensing with metal sensing surface and physically touching the metal sensing surface.

13. The head-mounted illuminator system of claim 1, wherein non-contact sensing with metal sensing surface is used for LED ON/OFF control and physically touching the metal sensing surface is used for one or more mode-setting functions.

14. The head-mounted illuminator system of claim 13, wherein the one or more mode-setting functions includes proximity control distance adjustment.

15. The head-mounted illuminator system of claim 14, wherein the LED illuminator is used to provide optical feedback to a user regarding mode-setting or distance adjustment junctions.

16. The head-mounted illuminator system of claim 15, wherein the LED illuminator comes ON, turns OFF or flashes in conjunction with the mode-setting or distance adjustment junctions.

17. The head-mounted illuminator system of claim 1, wherein the metal sensing surface forms part of a headband.

18. The head-mounted illuminator system of claim 1, wherein the metal sensing surface forms part of eyeglass frames.

* * * * *